United States Patent [19]

Gavlin et al.

[11] 3,959,371

[45] May 25, 1976

[54] PROCESS FOR THE PURIFICATION OF N,N-DIMETHYLACETAMIDE

[75] Inventors: Gilbert Gavlin, Lincolnwood; Abid Hashim Bengali, Chicago, both of Ill.

[73] Assignee: Custom Organics, Inc., Chicago, Ill.

[22] Filed: Oct. 8, 1974

[21] Appl. No.: 513,106

[52] U.S. Cl.............................. 260/561 R; 203/67; 203/69; 260/561 R; 203/37
[51] Int. Cl.²................ B01D 3/34; C07C 102/04; C07C 103/34
[58] Field of Search.............. 203/36, 69; 260/561 R

[56] References Cited
UNITED STATES PATENTS 2,156,642   5/1939   Slagh .............................. 260/561 A
2,953,503   9/1960   Freure .............................. 203/69 X

*Primary Examiner*—James H. Tayman, Jr.
*Attorney, Agent, or Firm*—John L. Hutchinson

[57] ABSTRACT

The present invention relates to the recovery of N,N-dimethylacetamide from a mixture containing N,N-dimethylacetamide and acetic acid. Potassium hydroxide is added to the mixture to neutralize the acetic acid and form potassium acetate having a low solubility in N,N-dimethylacetamide and a high affinity for water. The water concentration is adjusted to a desired range and a water non-solvent such as benzene is added to effect separation of an aqueous solution of potassium acetate from the dimethylacetamide as two distinct phases. The phases are then separated and the dimethylacetamide removed from the solvent phase by distillation.

5 Claims, No Drawings

PROCESS FOR THE PURIFICATION OF N,N-DIMETHYLACETAMIDE

DESCRIPTION OF THE INVENTION

Several methods for the production of N,N-dimethylacetamide involve the reaction of dimethylamine in the presence of water with acetic acid or methyl or ethylacetates. Such methods result in mixtures containing relatively large quantities of acetic acid. Due to what has been termed "the hydrogen bonding effect" acetic acid and N,N-dimethylacetamide form a mixture which cannot be readily separated. In the presence of acetic acid, N,N-dimethylacetamide acts as a base exerting a strong attraction for the acid. As a result of the above phenomenon, the acid and the amide form a high boiling azeotrope containing about 21.1 percent acetic acid and having a boiling point at 170.3° C.

Low boiling azeotropes are frequently used in fractionation procedures to separate liquid mixtures. Such azeotropic distillation has found little application however for splitting the N,N-dimethylacetamide-acetic acid complex. The equilibrium constant for dissociation of the complex does not provide sufficient free acetic acid over a wide range in temperature to permit efficient separation in the form of a lower boiling acetic acid azeotrope. When this procedure is attempted, it is observed that as acetic acid is removed the remaining acetic acid is more tightly bound in the complex and increasingly more difficult to separate. Furthermore, if any basic impurities are present such as dimethylamine they are more difficult to separate by distillation in the presence of acetic acid.

One solution to the separation of the N,N-dimethylacetamide and acetic acid is proposed in the patent to Freure 2,953,503, dated Sept. 20, 1960. According to the patent disclosure, separation may be accomplished by heating a mixture of the dimethylacetamide and acid in the presence of a non-polar solvent, such as a substituted benzene, to a temperature sufficient to vaporize the acetic acid and solvent. The dimethylacetamide is recovered in the residue. Suggested as additional non-polar solvents are chlorobenzene and the lower alkylbenzenes, such as toluene, ethylbenzene and the xylenes.

One of the problems encountered in a process of the type proposed in the above patent relates to the fact that the solvents should be used in quantities amounting to from about 100 – 500% of the mixture whose components are to be separated. Distillation of such large quantities of solvent is not considered economical. Further, in view of the fact that the most efficient solvents boil relatively close to N,N-dimethylacetamide, separation by fractional distillation must be carefully controlled.

Sodium hydroxide has been proposed for use in neutralizing the acetic acid in a mixture with N,N-dimethylacetamide and permit the latter to be distilled off. However, this process has not been used extensively outside of the laboratory for several reasons. First, sodium acetate and its hydrate are very soluble in dimethylacetamide making separation difficult. Second, as the dimethylacetamide is distilled, accumulation of solid sodium acetate prevents good heat transfer and also creates handling difficulties that result in losses of the dimethylacetamide. Further, if a sodium acetate non-solvent, such as xylene, is added to the separation process, it is possible to obtain a partial separation but not one that is readily suitable for commercial production. The solubility of sodium acetate trihydrate in dimethylacetamide remains high, of the order of 13 – 15 percent, even in the presence of a large quantity of the non-solvent. From relatively dry solutions sodium acetate in excess of this quantity will precipitate as the crystalline trihydrate and must be filtered with accompanying loss of dimethylacetamide. If excess water is added with the non-solvent, a two phase system is established, however, no separation of dimethylacetamide from sodium acetate and water is effected. The lower layer will be found to be the principal layer and to contain all of the water, all of the sodium acetate and about 90% of the dimethylacetamide. The upper layer is virtually entirely xylene and will contain about 10% of the dimethylacetamide. The net result of such a process is that it fails completely in the separation of dimethylacetamide from sodium acetate and all of the original problems persist.

It has been discovered that the use of potassium hydroxide to neutralize the acetic acid in a mixture of acetic acid and N,N-dimethylacetamide produces a completely different result as compared to the use of sodium hydroxide. More particularly, potassium acetate has a low solubility in dimethylacetamide, does not form a trihydrate and has a high affinity for water.

In the presence of water and even in the absence of a water non-solvent such as xylene, potassium acetate has been found to have a pronounced tendency to separate from dimethylacetamide as a second layer of concentrated aqueous solution. If a water non-solvent is present, this separation will be found to be more marked. Formation of a cleanly defined aqueous layer in this manner offers a great advantage in the separation process and improved recovery of the dimethylacetamide. Also, since potassium acetate has little tendency to be retained by dimethylacetamide the separation process can be completed without interference from precipitating solid salts.

In the purification process sufficient potassium hydroxide should be added to a mixture of acetic acid and N,N-dimethylacetamide to completely neutralize the acetic acid present. The neutralization temperature should be maintained below 50° C. and, preferably between about 25° C. to 40° C. to avoid possible hydrolysis of the dimethylacetamide. Either before or after neutralization, the water content of the mixture should be adjusted so that the final potassium acetate to water ratio covers a range of from about 1/1 to about 3/1 by weight, with a preferred ratio of about 2/1. If too much water is present, the dimethylacetamide will tend to dissolve in the water layer whereas, if too little water is used, the overall separation process will be appreciably slowed.

In addition, an organic non-polar water non-solvent is preferably added which also is a strong solvent for the dimethylacetamide, as distinguished from a compound which may be merely miscible with the dimethylacetamide. In general, such a solvent is added in the ratio of about 25% to 50% by volume of the dimethylacetamide. Exemplary solvents are benzene and the lower alkyl substituted benzenes, such as toluene, ethylbenzene and the xylenes.

Following adjustment of the water content and addition of the organic solvent, separation of two independent phases is clearly established, the water phase containing substantially all of the potassium acetate and the organic solvent or nonaqueous phase containing substantially all of the N,N-dimethylacetamide. The water phase will be the lower layer and may then be removed by either gravity separation or automatic decantation. In some instances, it may be necessary to wash the water phase with the solvent to remove a portion of the dimethylacetamide which may have dissolved in the aqueous layer.

The solvent phase may then be subjected to fractional distillation to remove the solvent and any water remaining leaving bottoms that are essentially pure N,N-dimethylacetamide. A final distillation may be employed to remove color impurities.

In general, it has been found that recovery of dimethylacetamide by the process of the present invention results in yields of about 85 – 95 percent and at considerable economic and time savings over prior art processes.

As further illustrating the invention, the following examples are presented.

EXAMPLE I

One hundred cc. of dry N,N-dimethylacetamide solution containing 9.5 percent by weight of acetic acid is neutralized with 13.4 cc. of commercial liquid potash (45% of 90% potassium hydroxide flake). The temperature during neutralization is maintained at about 35° C. A homogenous solution is formed of potassium acetate and dimethylacetamide. To this solution is added 35 cc. of xylene solvent, whereupon an aqueous layer comprising 26 cc. separates containing the following component percentages by weight:

potassium acetate 48%
water 30%
dimethylacetamide 22%

The lower aqueous layer is separated by draining from a separatory funnel and then is washed twice with two 22 cc. portions of xylene to reduce the dimethylacetamide content to 5%.

The xylene washings and the solvent phase are combined and subjected to fractional distillation to effect separation of xylene, boiling at 143° C. from N,N-dimethylacetamide boiling at 166° C. at atmosphere pressure. 80 cc. of N,N-dimethylacetamide are recovered comprising about 88% of the initial quantity in admixture with acetic acid. The distillate from a laboratory helix packed column having ten trays included an intermediate fraction of 21 cc. containing xylene and approximately 50% dimethylacetamide. This intermediate fraction may be used in subsequent dimethylacetamide recovery processes, in which case such subsequent recoveries are within the 90 – 95 percent range. The dimethylacetamide distillate residue contained no salt and was subject to simple distillation to make it water white.

EXAMPLE 2

One hundred cc. of dry N,N-dimethylacetamide solution containing 15 percent acetic acid is neutralized with 15.5 g. of commercial flake caustic potash (potassium hydroxide) at a temperature of 40° C. There is some tendency toward gel formation which is dispelled with the addition of 5 cc. of water. With this amount of water there is produced a small amount of a second liquid layer. On addition of 27 cc. of benzene, a water layer of 27 cc. separates cleanly from the dimethylacetamide solution. This water layer comprises 24 g. potassium acetate, 10 g. water, 3 g. dimethylacetamide. The water layer is washed with an equal volume of benzene and the dimethylacetamide is taken up completely. The dimethylacetamide-benzene solutions are combined and are stripped of benzene by distillation during which time the remaining water is also stripped. The benzene with a boiling point of 80° C. is readily fractionated cleanly from dimethylacetamide having a boiling point of 166° C. The residue is essentially pure dry dimethylacetamide. Distillation of this residue yields 8 g. of dimethylacetamide and leaves a semi-solid residue of 1–2 g.

Overall, the recovery of dimethylacetamide is about 95 percent based on the continued dimethylacetamide in the starting sample.

By way of further illustrating the advantages of this invention, the following example is presented of a process using sodium hydroxide.

EXAMPLE 3

One hundred cc. of dry N,N-dimethylacetamide solution containing 20 percent acetic acid is neutralized with commercial 50 percent sodium hydroxide. Approximately 31 g. (21 cc.) is required containing 15 g. of water. At this point, a dense gel sets up that would be substantially unmanageable in a commercial size reactor. The gel is eliminated by blending in an additional 3–4 percent of water. To cause separation of the sodium acetate, 50 cc. of xylene is added to the solution. Approximately 31 g. of sodium acetate trihydrate crystallizes out. On filtration, there is a loss of about 30 g. of dimethylacetamide as holdup with the crystals. Fractional distillation of xylene will leave a solution of sodium acetate in dimethylacetamide of about 65 cc. On stripping this solution to dryness, approximately 40 cc. of dimethylacetamide is recovered leaving a residue of 14 g. of sodium acetate and 10 g. of dimethylacetamide.

Overall, the recovery of dimethylacetamide is about 50–60 percent based on the contained dimethylacetamide in the starting sample.

Having described the invention and certain exemplary embodiments, the same is only intended to be limited by the scope of the following claims.

We claim:

1. A process for the separation of N,N-dimethylacetamide from a mixture of N,N-dimethylacetamide and acetic acid which comprises neutralizing the acetic acid with potassium hydroxide, adjusting the water content of the mixture whereby the water to potassium acetate ratio is between about 1/1 to 3/1 by weight, adding a non-polar water non-solvent and permitting the formation of an aqueous phase containing potassium acetate and a separate non-aqueous phase, separating the aqueous phase from the non-aqueous phase and subjecting the non-aqueous phase to distillation to remove the solvent.

2. A process as described in claim 1 wherein the water nonsolvent is member of the class consisting of benzene and the lower alkyl substituted benzenes.

3. A process as described in claim 2 wherein the solvent is benzene.

4. A process as described in claim 2 wherein the water to potassium acetate ratio is about 2/1 by weight.

5. A process as described in claim 2 wherein the water non-solvent is added in a ratio of about 25% to 50% by volume of the N,N-dimethylacetamide.

* * * * *